(12) United States Patent
Li (10) Patent No.: US 11,390,841 B2
(45) Date of Patent: Jul. 19, 2022

(54) CELL STRETCHING DEVICE

(71) Applicant: IFOM—FONDAZIONE ISTITUTO FIRC DI ONCOLOGIA MOLECOLARE, Milan (IT)

(72) Inventor: Qingsen Li, Milan (IT)

(73) Assignee: IFOM—FONDAZIONE ISTITUTO FIRC DI ON ONCOLOGIA MOLECOLARE, Milan (IT)

(*) Notice: Subject to any disclaimer, the term of this patent is extended or adjusted under 35 U.S.C. 154(b) by 110 days.

(21) Appl. No.: 16/479,146

(22) PCT Filed: Feb. 13, 2018

(86) PCT No.: PCT/EP2018/053477
§ 371 (c)(1),
(2) Date: Jul. 18, 2019

(87) PCT Pub. No.: WO2018/149795
PCT Pub. Date: Aug. 23, 2018

(65) Prior Publication Data
US 2019/0390152 A1    Dec. 26, 2019

(30) Foreign Application Priority Data
Feb. 15, 2017  (EP) ..................... 17156179

(51) Int. Cl.
*C12M 1/42* (2006.01)
*C12M 1/36* (2006.01)

(52) U.S. Cl.
CPC ............ *C12M 35/04* (2013.01); *C12M 41/48* (2013.01)

(58) Field of Classification Search
CPC .............................. C12M 35/04; C12M 41/48
See application file for complete search history.

(56) References Cited

U.S. PATENT DOCUMENTS 5,321,109 A * 6/1994 Bosse ..................... B29C 55/10
428/910
5,348,879 A * 9/1994 Shapiro .................. C12M 35/04
435/29

(Continued)

FOREIGN PATENT DOCUMENTS

| WO | 00/17317 A1 | 3/2000 |
| WO | 2006/072911 A1 | 7/2006 |
| WO | 2014/085933 A1 | 6/2014 |

OTHER PUBLICATIONS

Kamble, Harshad; et al., "Cell stretching devices as research tools: engineering and biological considerations", Lab on a Chip, Royal Society, of Chemistry, vol. 16, No. 17, 2016, pp. 3193-3203.

(Continued)

*Primary Examiner* — William H. Beisner
*Assistant Examiner* — Danielle B Henkel
(74) *Attorney, Agent, or Firm* — Lucas & Mercanti, LLP (57) ABSTRACT

A cell stretching device including a cell chamber having upper and lower portions is disclosed. The lower portion has fixing means for fixing a deformable cell substrate (S) to the cell chamber and defining a stretching region inside the chamber at the lower portion. The upper portion has stretching means movable relative to the chamber and acting on the cell substrate (S) and a support element for holding the stretching means and a driving unit coupled to the upper portion of the cell chamber and engageable to the stretching means for mechanically controlling and regulating the movement of the stretching means relative to the cell chamber. The stretching means include clip members operating inside the stretching region which are configured to clamp the cell substrate (S) at a clamping contact point and to stretch the cell substrate (S) in response to the movement.

9 Claims, 11 Drawing Sheets

(56) References Cited

U.S. PATENT DOCUMENTS

| | | | | |
|---|---|---|---|---|
| 5,406,853 | A * | 4/1995 | Lintilhac | G01N 3/02 |
| | | | | 73/789 |
| 6,576,458 | B1 * | 6/2003 | Sarem | C12M 23/34 |
| | | | | 435/286.5 |
| 6,586,235 | B1 * | 7/2003 | Banes | C12M 23/10 |
| | | | | 435/293.1 |
| 6,998,265 | B2 * | 2/2006 | Banes | C12M 25/14 |
| | | | | 435/305.1 |
| 9,493,735 | B2 * | 11/2016 | Yoo | C12M 35/04 |
| 2007/0178584 | A1 * | 8/2007 | Naruse | C12M 23/26 |
| | | | | 435/289.1 |
| 2008/0166796 | A1 * | 7/2008 | Quinn | C12M 25/02 |
| | | | | 435/289.1 |
| 2012/0208229 | A1 * | 8/2012 | Rubner | B01L 3/505 |
| | | | | 435/29 |
| 2012/0219981 | A1 * | 8/2012 | Muthiah | C12M 35/04 |
| | | | | 435/29 |
| 2013/0105348 | A1 * | 5/2013 | Koob | A61L 27/3804 |
| | | | | 206/438 |
| 2017/0121661 | A1 * | 5/2017 | Gasset | C12N 13/00 |
| 2017/0175078 | A1 * | 6/2017 | Makino | C08G 73/1039 |
| 2019/0093063 | A1 * | 3/2019 | Subramanian | A61L 27/54 |

OTHER PUBLICATIONS

Database WPI, XP002781534, Week 201259, CN202322860U, (Jiangsu Biomagsystem Medical Co., Ltd.), Jul. 11, 2012, Abstract, Thomson Scientific, London, GB (8 pages).
ISA/EP, PCT International Search Report and Written Opinion issued in connection with PCT/EP2018/053477, dated Jun. 11, 2018 (14 pages).

* cited by examiner

CELL STRETCHING DEVICE

CROSS-REFERENCE TO RELATED APPLICATIONS

This application is a 371 of PCT/EP2018/053477, filed Feb. 13, 2018, which claims the benefit of European Patent Application No. 17156179.8, filed Feb. 15, 2017.

TECHNICAL FIELD

The present invention relates to a cell stretching dish or more generally a cell stretching device for stretching biological cells plated on a deformable cell substrate. The invention also relates to a kit for cell stretching comprising a cell stretching device and a deformable substrate.

BACKGROUND

Cells in the body constantly experience mechanical stimuli in various organ movement, development and functions. These mechanical stimuli are often essential to proper cell function, such as migration, proliferation, differentiation (Engler, Sen et al. 2006, Cell 126(4): 677-689; Vogel and Sheetz 2006, Nat Rev Mol Cell Biol 7(4): 265-275; Chen 2008, J Cell Sci 121 (Pt 20): 3285-92; Wozniak and Chen 2009, Nat Rev Mol Cell Biol 10(1): 34-43). Cells sense such mechanical stimuli through a process called mechanotransduction (Chen 2008 J Cell Sci 121 (Pt 20): 3285-92; Wang, Tytell et al. 2009 Nat Rev Mol Cell Biol 10(1): 75-82; Shivashankar 2011). Abnormal mechanotransduction leads to several pathogenesis, such as cancer, asthma, heart disease (Chen 2008 Chen 2008 J Cell Sci 121 (Pt 20): 3285-92; Jaalouk and Lammerding 2009, Nat Rev Mol Cell Biol 10(1): 63-73.; DuFort, Paszek et al. 2011, Nat Rev Mol Cell Biol 12(5): 308-19). Mechanotransduction has attracted great interest from many clinicians and scientists for better understanding of medical pathology and improving clinical diagnosis (Iskratsch, Wolfenson et al. 2014, Nat Rev Mol Cell Biol 15(12): 825-833).

In Mechanobiology studies, the advance of in vitro technologies for the application of physiologically mimicking mechanical force to cultured cells and tissue are vital due to the complex in vivo biological system. The growing interest in mechanobiology and technology gap have motivated the development of cell stretching device in various research labs and companies (Kamble, Barton et al. 2016, Lab on a Chip 16(17): 3193-3203).

US 2012/219981 discloses a mechanical stretching device with a stretchable substrate and two engagement areas located at opposite ends of the stretchable substrate. The stretching is performed by two motors such that the substrate is stretched along opposite directions with respect to each other.

U.S. Pat. No. 6,107,081 discloses a unidirectional cell stretching device capable of mimicking linear loading profiles. The device comprises a ram, at least one strip, a tissue culture vessel, a sealed chamber and a mechanical pump, wherein the strips are connected to the ram by removable pins through a cylindrical tube support to form a ram assembly. The strips are elastic, and coated with an extracellular matrix upon which tissue cultured cells are grown and stretched. The pump is controlled by a microprocessor and regulates the amount of load placed upon the cells. Further, the ram moves bi-directionally in a single plane in an interval or continuous mode. Such a movement is driven by injecting a sterile fluid into the sealed chamber of the ram using the mechanical pump.

WO 00/17317 discloses a planar biaxial stretching device wherein both the stationary ring (to which the membrane is affixed) and the indentation ring are on the same side of the membrane, with the indentation ring smaller than (and inside) the stationary ring. When the indentation ring is pressed against the membrane to apply a biaxial stretch, the stretched portion of the membrane spans the rim of the indentation ring itself in a planar configuration.

Although known cell stretching devices can be very precise and efficient in their functioning, most of these systems are bulky and complicated in use, thereby comprising huge number of mechanical and electrical components. Furthermore, in several cases prior art stretching devices are limited in functions and are not designed for a multifunctional stretching process.

It is therefore an object of the present invention to provide a device that solves the abovementioned problems, in particular, to provide a cell stretching device that is efficient, simple to use, reduced in size and able to perform different stretching functions (uniaxial, biaxial, high level stretch, high resolution imaging) on cells for high resolution imaging.

This object is achieved by the cell stretching device and the kit according to the independent claims. Further advantageous combinations and designs are given in the dependent claims therefrom.

SUMMARY OF THE INVENTION

The cell stretching device according to the present invention comprises a cell chamber having an upper portion and a lower portion, wherein the lower portion of the chamber comprises fixing means for fixing a deformable cell substrate to the cell chamber and defining a stretching region inside the chamber at the lower portion. The upper portion comprises stretching means movable relative to the chamber and acting on the cell substrate and a support element for holding the stretching means.

In addition, the cell stretching device comprises a driving unit coupled to the upper portion of the cell chamber and engageable to the stretching means for mechanically controlling and regulating the movement of said stretching means relative to the cell chamber.

In particular, the cell stretching device is characterized in that the stretching means comprise clip members operating inside the stretching region, the clip members being configured to clamp the cell substrate at a clamping contact point and to stretch said cell substrate in response to the movement of the stretching means relative to the cell chamber.

With respect to prior art stretching devices, the device according to the present invention is simpler to use. In fact, in order to stretch the cell substrate, the device comprises clip members that are in direct contact with the substrate and simply clamp it at a particular clamping contact point and stretch it in response to the movement of the stretching means. Furthermore, the device is more compact and consequently easily maneuverable compared to known stretchers. In fact, the stretching means and therefore the clip members, operates within the stretching region that is a limited area defined by the fixing means at the lower portion of the cell chamber.

In this contest, the fixing means can be any element or combination of elements apt to keep the cell substrate planar and under tension.

The cell substrate can be any stretchable membrane on which biological cells can be grown. For example, the cell substrate can be a transparent silicone elastic membrane or the like. Such a membrane can have a thickness comprised between 300 μm and 100 μm, in particular 127 μm, for example for microscopes with oil or water immersion objectives.

Advantageously, the mechanical control and regulation of the stretching means can be done manually or automatically. The user can actuate the driving unit by simply handle a mechanical actuator, thereby strongly reducing sophisticated components. Moreover, it is also possible to provide the stretching device with a motor coupled to the driving unit and programmed to mimic cyclic stretch in all kinds of physiological conditions.

The clip members can be formed by a clamp element located at an extremity of the stretching means and a removable pin engageable with the clamp element, so that the cell substrate can be interposed between the clamp element and the pin, thereby forming a clamping contact point. Based on this particular clamping configuration, a better and more efficient grabbing of the cell substrate is assured. In particular, this grabbing process can be performed at any point within the stretching region. Differently from prior art devices where the substrate is stretched pulling from the extremities or is subject to complicated indentation processes, the device according to the present invention provide a simple and precise method for stretching a particular and dedicated area of the cell substrate.

According to one embodiment of the present invention, the clip members are located at least in part inside the cell chamber and interact with only the side of the cell substrate facing inward the cell chamber.

In this way, the side of the cell substrate facing outward the cell chamber represents the bottom of the device. Differently from the known cell stretching devices, the stretching means do not interfere with the external part of cell substrate that is, on the other hand, freely accessible to microscope objectives. In particular, the device according to the present invention is compatible with high resolution objectives, such as short working distance oil or water immersion objectives, for live cell as well as fixed cell immunofluorescence imaging and can be scaled up and down to fit any inverted microscope.

According to the present invention, the stretching means are engageable to the driving unit to define the initial position of a clamping contact point of the clip members on the cell substrate. In particular, the stretching means must be positioned centrosymmetric to the centre of the chamber for the precise engagement of the driving unit, therefore, driving unit is engaged to the stretching means in the first place to facilitate the determination of initial contact point.

In this way, the stretching means and therefore the clip members can be initially positioned on the cell substrate at different clamping contact points based on the actuation of the driving unit. In other words, the level of stretching can be varied as a function of these initial clamping contact points. For example, the stretching means can be positioned in order to clamp and stretch the central portion of the cell substrate by the clip members. The maximum level of stretch can be increased easily by simply reducing the preset of the initial distance between the clip members. Compared to known cell stretchers, which only allow a low level of stretch (<30% strain) the cell stretcher according to the present invention can reach a strain of 100% or more.

In a preferable embodiment of the present invention, the stretching means comprise at least a pair of opposing arms movable apart from each other.

In case the device comprises only two opposing arms and therefore two opposing clip members, the stretching means will provide a uniaxial stretch of the substrate.

On the other hand, in case the device comprises four opposing arms and therefore four opposing clip members, the stretching means can provide a biaxial stretch of the substrate, if the two opposite stretching direction are orthogonal. This clearly shows the versatility of the device of the present invention that can provide a dual function: uniaxial and biaxial stretch.

Specifically, each arm can be L-shaped having a first extremity fixable to the support element of the cell chamber and a second extremity comprising the clip member.

In a further embodiment of the present invention, the stretching means are detachable from the cell chamber.

In this way, it is possible to transform the stretching device able to perform a biaxial stretch (having for example two pairs of opposing stretching means) into a stretching device able to perform a uniaxial stretch (having for example a single pair of opposing stretching means), by simply detaching a pair of opposing stretching means from the cell chamber. Similarly, it is possible to transform the device from a uniaxial to a biaxial stretching system by attaching a pair of opposing stretching means.

According to an embodiment of the present invention, the driving unit comprises driving means to be actuated by a user for producing a driving movement and transfer means coupled to the driving means to transfer the driving motion to the stretching means.

By actuating the driving means, the user is able to control and regulate the movement of the stretching means and then apply the required strain to the cell substrate.

In particular, the driving means can comprise a turning knob provided with a worm gear and a cogged ring engageable with the worm gear.

The presence of a turning knob facilitates the driving movements for the user. The turning knob can also be connected to a motor for automatic control. The movement is transferred to the stretching means through a simple gear system (worm gear, cogged ring, . . . ).

Also, the transfer means can comprise at least a pair of slidable hinges and a coupling supporting element, each hinge having an extremity fixable to the driving means and the other extremity fixable to the corresponding stretching means.

In this case, a sliding mechanism facilitates the transfer of the driving movement in one direction and the return in the opposite direction. In particular, the hinges can have a bent shape and can be provided with a pin fixed to a rotatable element (for example the cogged ring) and a pin linearly sliding inside a linear slot and fixable to the stretching means so as to allow the transfer of the rotational movement of the rotatable element to the linear movement of the stretching means and vice versa.

In another embodiment of the present invention, the fixing means comprise a cylindrical ring and a hoop engageable with the ring in order to fix the cell substrate to the cell chamber so that the substrate is planar and under tension.

The cell substrate can be first positioned on the cylindrical ring and then can be fixed by engaging the hoop to the ring, the substrate being blocked at the edge between the hoop and the ring. In this way, the cell substrate assumes a planar configuration.

In still another embodiment of the invention, the cell chamber and the driving unit comprise each a through hole in the center of the device.

This is extremely useful in order to facilitate the microscope imaging of the cells during the stretching experiment as well as exchange of medium and drug treatment. Advantageously, the device can be provided with a small circle with a through-hole as a reference to facilitate focus on the center of the stretching region during the experiment.

According to a further embodiment of the present invention, the device has a circular shape that can be scaled down a diameter less than 10 cm.

In this way, the device according to the present invention is reduceable to the size of a cell culture dish. In particular, the device can be configured to be contained in a 10 cm cell culture Petri dish.

In a preferable embodiment of the present invention, all the components of the cell chamber and of the driving unit are made of a plastic or other material suitable to be printed by means of a 3D-printer. This implies that the device can be mass produced easily by other industrial process and using different material.

This further reduces the cost of production, bringing down the complicated cell stretching system to a consumable level.

That also means that the device can be designed to be modular based on function and that each component can easily be replaced and reassembled.

The components of the device can also be made of different materials which are not necessary apt to be printed with a 3D printer but are suitable for the purpose of the present intention.

The kit for cell stretching according to the present invention comprises a cell stretching device according to any of the preceding claims and at least a stretchable cell substrate for growing cultured cells.

Also, the kit can comprise a small circle with a through-hole to be put on the top of the device as a reference point for the stretching experiments.

The device and the kit according to the present invention is designed and configured to be utilized for different applications and under different conditions. In particular, the cell stretching device is designed for high resolution, live cell as well as fixed cell immunofluorescence imaging for variety of cell experiments requiring mechanical stimuli (uniaxial and biaxial stretch). Specifically, to study cell morphology/cytoskeleton/nucleus/stretch sensitive ion channel/transcription factor/gene expression under mechanical stretch condition. Also, the cell stretching device can be customized to be integrated with Atomic Force Microscope (AFM) as a powerful extension.

The cell stretching device can be minimized in size and integrated with imaging analysis instruments for disease diagnosis and drug testing.

Furthermore, the device can be used in combination with other techniques for advanced research tools such as for example: micropillars/gel traction force (single cell measurement, cell/nuclear stiffness screening); micropattern (cell shape transformation); cell lateral compression experiment; step increasing cell stretching to study cell adaptation to mechanical stress; polarized substrate stiffness by uniaxially pre-stretch soft substrate.

In addition, the design can be modified (i.e. the design can be inverted) and adapted to fit high resolution upright microscopes.

The cell stretching device can also be adapted to stretch 3D culture sample and tissue samples.

The present disclosure also describes a cell stretching device comprising a stretching means carrier and a disposable membrane carrier couplable to the stretching means carrier. It is noted that the components of this device are almost the same of the cell stretching device described above. Therefore for a detailed description of the single components, reference is made to the above disclosure. In particular, the disposable membrane carrier comprises fixing means and a deformable cell substrate. Specifically, the membrane carrier can comprise any element or combination of elements apt to keep the cell substrate planar and under tension. For example, the disposable membrane carrier can comprise a cylindrical ring and a hoop engageable to the ring (i.e. by clamping) in order to fix the cell substrate to the ring. In other words, the membrane carrier is represented by a deformable cell substrate, or membrane, and fixing means for keeping the cell substrate under tension.

The stretching means carrier comprises the stretching means and a support element for holding the stretching means, wherein the stretching means are movable relative to the fixing means and then to the cell substrate. Also, the stretching means carrier comprises a driving unit coupled to the support element and engageable to the stretching means for mechanically controlling and regulating the movement of the stretching means relative to the cell substrate. In particular, the stretching means comprise clip members configured to clamp the cell substrate at a clamping contact point and to stretch the cell substrate in response to the movement of the stretching means relative to the fixing means and then to the cell substrate. The stretching means carrier comprises a receiving region for receiving the membrane carrier and engaging it to the support element. Once the membrane carrier is engaged to the stretching means carrier to form the cell stretching device, it is created a stretching region inside which the stretching means operate.

The membrane carrier is particularly suitable to be coupled to a stretching means carrier in which the clip members interact with only one side of the cell substrate and in particular with the side facing inwardly. The side of the cell substrate facing outwardly represents the bottom of the device and can be freely accessible to microscope objectives.

Advantageously, the membrane carrier is disposable and can be easily engaged to and disengaged from the stretching means carrier through a coupling mechanism present in dedicated portions of these two carriers. The engagement can be performed by inserting the membrane carrier into the receiving region of the stretching means carrier. For example, the receiving region can be represented by an aperture (i.e. circular) of the support element, wherein the coupling mechanism can be placed on the support element of the stretching means carrier and on the fixing means, particularly on the cylindrical ring, of the membrane carrier. In other words, a user can employ the same stretching means carrier with different membrane carriers. Once the cells have been stretched on a membrane carrier and experimental results have been analyzed, this membrane carrier can be set aside and a new membrane carrier can be utilized for the next experiment.

The engagement between the membrane carrier and the stretching means carrier can occur by a snap-fit coupling mechanism by inserting a portion of the membrane carrier into the receiving region of the stretching means carrier. However, the coupling mechanism can comprise particular engaging elements. For example, the upper border of the fixing means, i.e. the upper border of the cylindrical ring, can be provided with one or more teeth or recesses and the internal part of the support element can be provided with one or more corresponding recesses or teeth engageable with the teeth or recesses of the fixing means.

In this way, the engagement between the membrane carrier and the stretching means carrier results more stable. In particular, the coupling mechanism can be configured in such a way that the contact between the stretching means and the cell substrate is improved.

Of course other coupling mechanisms can be conceivable in order to reach the same results.

Specifically, the present invention comprises the following aspects:

(1) A disposable membrane carrier couplable to a stretching means carrier for stretching cells, the membrane carrier comprising a stretchable cell substrate for growing cultured cells and fixing means for supporting the cell substrate and keeping said cell substrate under tension, wherein the membrane carrier further comprises coupling means for the engagement to and the disengagement from the stretching means carrier.

(2) The disposable membrane carrier according to aspect 1, wherein the cell substrate has an upper side and a bottom side opposite to the upper side and the coupling to the stretching means carrier is performed in such a way that the stretching means carrier faces only the upper side of the cell substrate.

(3) The disposable membrane carrier according to one of the preceding aspects, wherein the fixing means is couplable to the stretching means carrier through a snap-fit mechanism.

(4) The disposable membrane carrier according to one of the preceding aspects, wherein the fixing means comprise a cylindrical ring and a hoop engageable with the ring.

(5) The disposable membrane carrier according to aspect 4, wherein the cylindrical ring is provided with inserting coupling means.

(6) The disposable membrane carrier according to aspect 5, wherein the inserting coupling means comprise at least a tooth or projection.

(7) A stretching means carrier couplable to a disposable membrane carrier for cell stretching, the stretching means carrier comprising stretching means movable relative to the membrane carrier, a support element for holding the stretching means, and a driving unit coupled to the support element and engageable to the stretching means for mechanically controlling and regulating the movement of said stretching means, wherein the stretching means carrier comprises furthermore coupling means for the engagement to and the disengagement from the disposable membrane carrier.

(8) The stretching means carrier according to aspect 7, wherein the coupling to the disposable membrane carrier is performed in such a way that the stretching means face only one side of the membrane carrier.

(9) The stretching means carrier according to one of the preceding aspects, wherein the stretching means comprise clip members, the clip members being configured to clamp the disposable membrane carrier at a clamping contact point and to move in response to the movement of the stretching means relative to the membrane carrier.

(10) The stretching means carrier according to one of the preceding aspects, wherein the support element is coupled to the disposable membrane carrier through a snap-fit mechanism.

(11) The stretching means carrier according to one of the preceding aspects, wherein the support element is provided with receiving coupling means.

(12) The stretching means carrier according to aspect 11, wherein the receiving coupling means comprise at least a recess.

(12) A cell stretching device comprising the disposable membrane carrier according to one of the aspects between 1 and 6 and the stretching means carrier according to one of the aspects between 7 and 11.

BRIEF DESCRIPTION OF THE DRAWINGS

Preferred embodiments of a cell stretcher device in accordance with the invention will be explained herein below in greater detail with reference to the accompanying drawings, in which.

DETAILED DESCRIPTIONS OF THE INVENTION

Figure 1A:
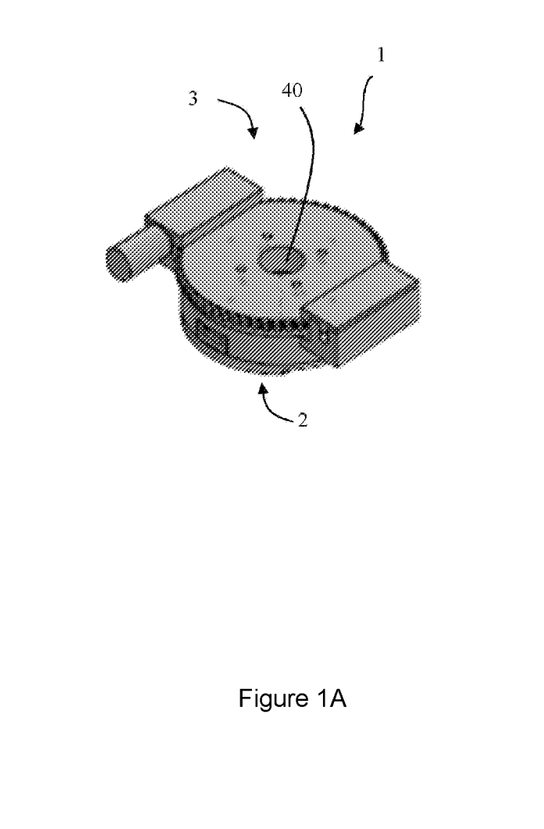
FIGS. 1 and 1b show a perspective view of the cell stretching device according to the present invention in an assembled configuration (a) and in an exploded configuration (b)

FIG. 1a describes the cell stretching dish or more generally the cell stretching device 1 in an assembled configuration.

The device 1 comprises a cell chamber 2 forming the bottom of the device 1 and a driving unit 3 forming the top of the device 1. The driving unit 3 is joint to the cell chamber 2 for example by a snap-fit way. Other fixing means are of course conceivable. The device 1 is provided with a through hole 40 in order to facilitate the microscope imaging of the cells during the stretching experiment as well as exchange of medium and drug treatment.

Figure 1B:
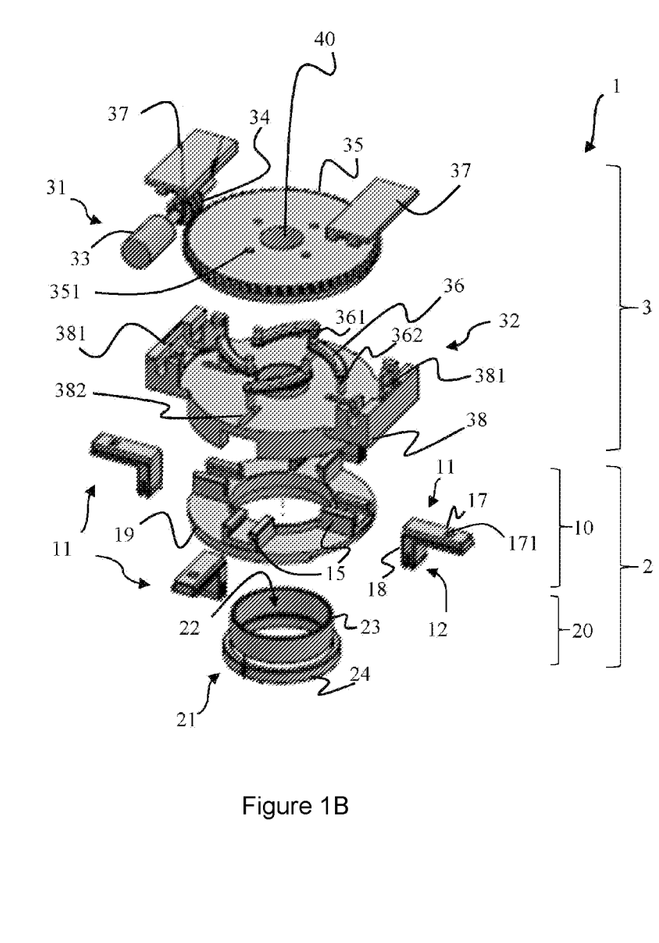

FIG. 1b describes the cell stretching device 1 in an exploded configuration. It is worth to notice that each single component shown in the figure can be disassembled and reassembled to form the device 1 by simply snap-fitting each component to the other, without the use of any attaching means, such as glue, screws, or the like.

The single parts can be made of plastic or other materials. In particular, the cell stretching device can be designed using a dedicated CAD software and the components can be 3D printed and assembled. The components can be printed using Dental SG resin for its biocompatibility and then washed by IPA for 20 minutes, followed by post processing in UV chamber. Before the assembling, the processed components can be further polished.

The cell chamber 2 is formed by an upper portion 10 and a lower portion 20.

The lower portion 20 comprises fixing means 21 formed by a cylindrical ring 23 and a hoop 24 that is engageable with the ring 23. In particular, a stretchable silicon membrane (not shown in the figure) can be clamped by the cylindrical ring 23 and the hoop 24 to form the deformable cell substrate S. Once the membrane is fixed to the ring 23, within the fixing means 21, and in particular within the cylindrical ring 23, a stretching region 22 is defined, where the cell substrate S is planar and under tension.

The upper portion 10 comprises a support element 19 having the shape of a ring and four stretching means 11 fixable to the support element 19 at four equidistant points opposed to each other in pairs. In particular, the stretching means 11 are L-shaped arms 16 having a first extremity 17 insertable into a receiving means (slot) 15 located on the support element 19. In this case, the arm 16 of the stretching means 11 can slide into the slot of the receiving means 15 and can be fixed at a determined position. The second extremity 18 of the stretching means 11 comprises clip members 12 which point downward inside the cell chamber 2 within the stretching region 22.

The driving unit 3 comprises a driving means 31 composed by a worm gear 34 provided with a turning knob 33 and a cogged ring 35 engageable with the worm gear 34. The driving unit 3 also comprises a transfer means 32 composed by a coupling supporting element 38 and four hinges 36 having an arcuate shape.

It is noted that the each hinge 36 comprises at one extremity a top pin 361 and at the other extremity a bottom pin 362. The top pin is configured to be insertable into one of the ring holes 351 present in the cogged ring 35 close to the through hole 40. On the other hand, the bottom pin 362 is configured to be insertable into a dedicated stretching element hole 171 present in the first extremity 17 of each stretching means 11 passing through a corresponding linear slot 382 present in the coupling supporting element 38.

In addition, the device 1 comprises two caps 37 that serve to firmly fix the driving means 31 to the transfer means 32 through a snap-fitting with two corresponding engagement members 381 present on the coupling supporting element 38.

In an assembled configuration, the hoop 24 is engaged with the cylindrical ring 23 to form the fixing element 21 and the cell substrate S is clamped to form a stretching region 22. The four stretching means 11 are inserted to the support element 19 in the corresponding receiving means 15. The stretching means 11 can slide inside of the receiving means 15, the initial position of stretching means 11 being determined with the help of engaging driving unit 3. The upper part of the cylindrical ring 23 is then inserted in the central hole of the support element 19, thereby forming the cell chamber 2. In this configuration, the second extremity 18 of each stretching means 11, that is each clip member 12, is in contact with the cell substrate S.

The worm gear 34 is engaged with the edge of the cogged ring 35 and the top pins 361 of each hinge 36 is inserted in the corresponding ring hole 351, whereas the bottom pins 362 of each hinge 36 is inserted in the corresponding stretching element hole 171 passing through the linear slot 382. The two caps 37 are snap fitted into the corresponding engagement members 381.

As a consequence of the actuation of the turning knob 33 by a user or motor, the cogged ring 35 rotates in one or the opposite direction. The rotational movement of the cogged ring 35 determines a corresponding displacement of the four hinges 36 and a translational movement of the stretching means 11 forwards, toward the center of the stretching region 22 or backwards based on the rotational direction of the cogged ring 35. In other words, the stretching of the cell substrate S is simply obtained by the actuation of the turning knob 33 in one direction. On the other hand, the release of the cell substrate S is obtained by the actuation of the turning knob 33 in the other direction.

Figure 2:
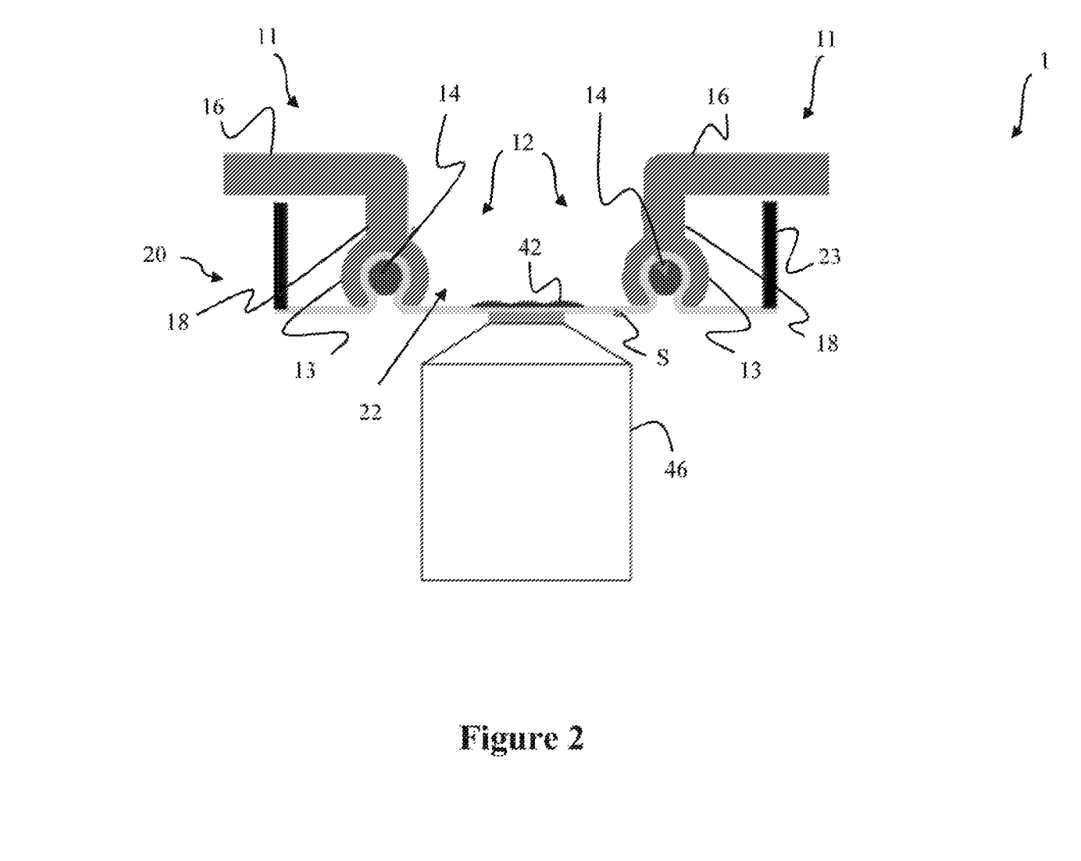
FIG. 2 shows a schematic representation of the lower portion of the cell chamber coupled to a microscope objective.

FIG. 2 describes a schematic representation of the device 1 coupled to the objective 46 of a microscope. In particular, the figure shows the lower portion 20 and two opposing stretching means 11 of the device 1. The second extremity 18 of the stretching means 11 is provided with clip members and specifically with a clamp element 13 and a pin 14. In order to clamp the cell substrate S, the substrate S is interposed between the clamp element 13 and the pin 14. In this way, the linear movement of the stretching means 11 in the opposite direction toward the edge of the stretching region 22 determines the stretching of the cell substrate S and consequently of the cells 42 present thereon. Since the clip members 12 interact with only the side of the cell substrate S facing inward the cell chamber 2, the other side of the cell substrate S is freely accessible to the objective 46 of any type of microscopes, the outer surface of the cell substrate forming the bottom surface of the device 1. This allows the employment of the device 1 for analyzing the stretching of the cells 42 using particular high resolution microscopes, such as apparatus having oil or water immersion objectives.

Figure 3A:
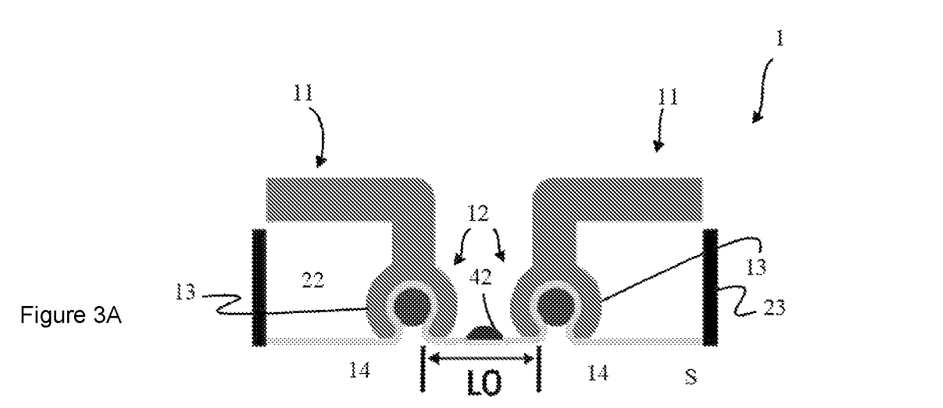
FIGS. 3a, 3b and 3c show a schematic representation of the functioning of the device according to the present invention when no stretching is applied (a), an intermediate level of stretching is applied (b) and a maximum level of stretching is applied (c)
Figure 3B:
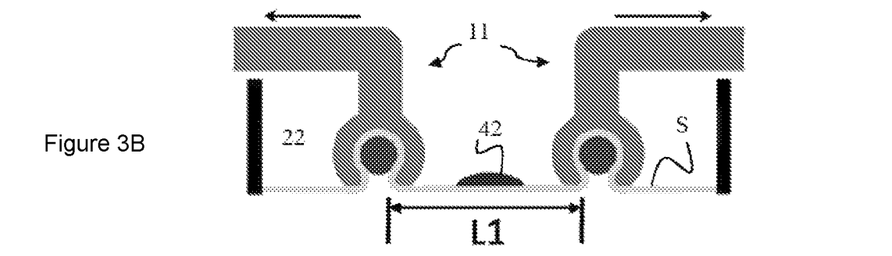
Figure 3C:
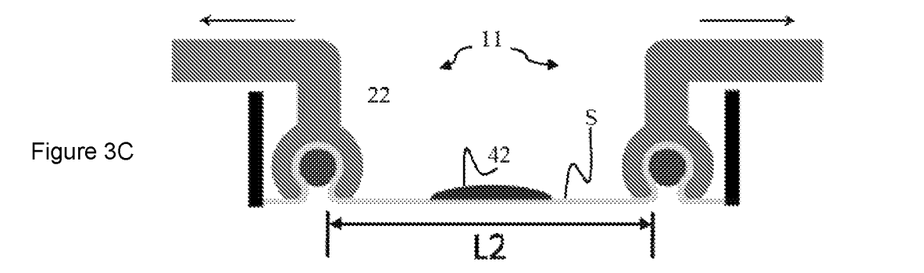

FIGS. 3a-3c describe the functioning of the cell stretching device 1. In particular, FIG. 3a shows an initial phase when the clip members 12 clamp the cell substrate S and no stretching action has been applied, that is when the turning knob 33 has not been actuated. In this initial phase, the distance between two opposing clip members 12 is set L0, close to the center of the stretching region 22. Based on this initial set distance, the cells 42 can be subjected to a greater of a lower stretching. FIG. 3b shows an intermediate phase after the turning knob 33 has been actuated. The distance between two opposing clip members 12 is now L1 and would correspond to a determined percentage of stretch of the cells 42. The clip members 12 are moved according to the arrows. FIG. 3c shows a final stretching phase after the turning knob 33 has been further actuated. The distance between two opposing clip members 12 is now L2 and represents the maximum stretch possible, since the clip members 12 have reached the edges of the stretching region 22. The maximum stretch can be increased by reducing the initial distance of opposing clip members 12 at L0.

Figures 4A, 4B:
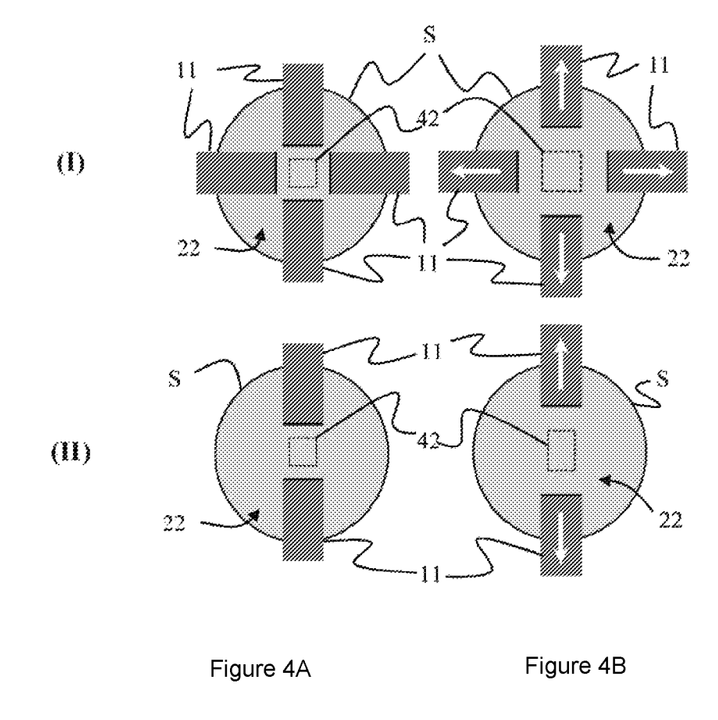
FIGS. 4a and 4b show a schematic representation of the cell chamber from above when no stretching is applied (a) and when stretching is applied (b) in case of biaxial (I) and uniaxial (II) stretching.

FIGS. 4a and 4b describe the different configurations of the cell stretching device 1 according to the present invention. The figures show a first configuration (I) in which four stretching means 11 are fixed to the support element 19 and a second configuration (II) in which only two stretching means 11 are fixed to the support element 19. Also, the figures show the initial phase (FIG. 4*a*) when no stretch is applied to the cell substrate S and the stretching phase (FIG. 4*b*) when a stretching action is applied to the cell substrate S.

As can be noticed in the figures, in the first configuration (I) the cell substrate S is stretched according to four opposing points in two directions (see the arrows in the FIG. 4*b*) and the cells 42 under analysis are subjected to a biaxial strain, thereby determining an homogeneous stretching action in two direction. This is evident by comparing the dashed regions of FIGS. 4*a* and 4*b*. On the other hand, in the second configuration (II) the cell substrate S is stretched according to two opposing points in one direction (see the arrows in the FIG. 4*b*) and the cells 42 under analysis are subjected to a uniaxial strain, thereby determining a longitudinal stretching action in one direction. Again, this is evident by comparing the dashed regions of FIGS. 4*a* and 4*b*.

Figure 5A:
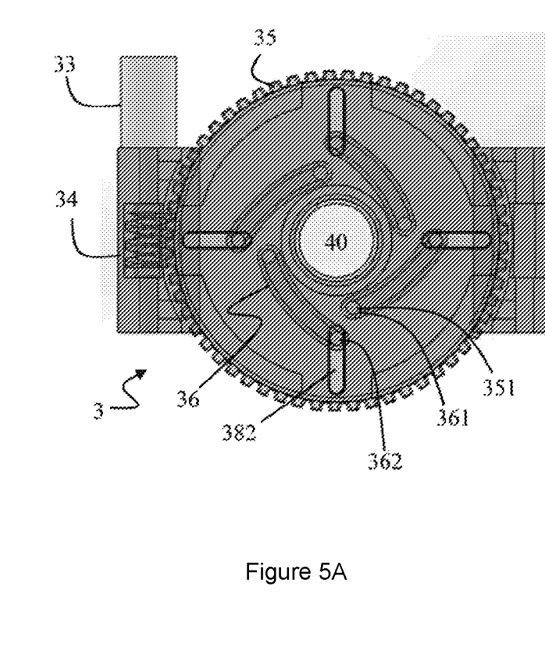
FIGS. 5a and 5b show a schematic representation of a part of the driving unit according to the present invention.
Figure 5B:
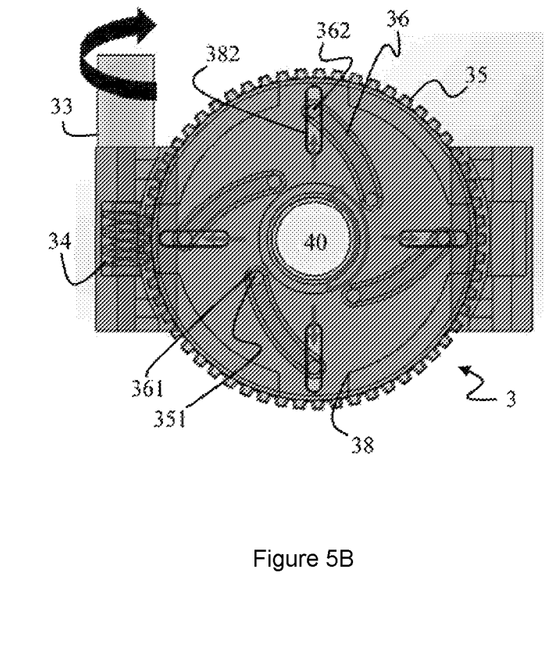

FIGS. 5*a* and 5*b* show how the actuation of the turning knob 33 affects the longitudinal movement of the stretching means 11. These figures are represented observing the device 1, and in particular the driving unit 3, from below with a certain grade of transparency of the different components composing the driving unit 3. FIG. 5*a* describes the initial phase when the knob 33 is not actuated and no stress is applied to the cell substrate S. The four hinges 36 are located between the cogged ring 35 and the coupling supporting element 38 and the bottom pins 362 are located at an edge of the linear slot 382. Specifically, the pins 362 are located at the edge closer to the center of the through hole 40. On the other hand, the top pins 361 are inserted in the corresponding ring holes 351. FIG. 5*b* describes a stretching phase when the knob 33 is actuated and rotated. In this case the cell substrate S is subjected to a certain stress. The actuation of the knob 33 determines a rotation of the cogged ring 35. Based on the presence of the four hinges 36, the rotation produces a movement of one extremity of the hinges 36 along the linear slot 382. This determines a longitudinal movement of the stretching means 11 which are fixed to the bottom pins 362 sliding along the linear slot 382. As a consequence of the rotational movement, the pins 362 are moved toward the other edge of the linear slot 382 closer to the border of the cogged ring 35. The arrows present in FIG. 5*b* clarify this concept.

The cell stretching device 1 according to the present invention has been tested using different cell types, the representative results are shown in FIGS. 6-9.

For cell culture and imaging experiment preparation, the cell chamber 2 was sterilized. In particular, the cell chamber 2 was plasma treated for 30 seconds and then coated with fibronectin (or required protein) for an hour. The cells 42 were then seeded into the cell chamber 2 and maintained in cell incubator. Before imaging, the cell chamber 2 was assembled with the driving unit 3 to form the cell stretching device 1.

Cell imaging was captured using 40× oil lens (NA=1.3) in Perkin Elmer spinning disk microscope.

Figure 6A:
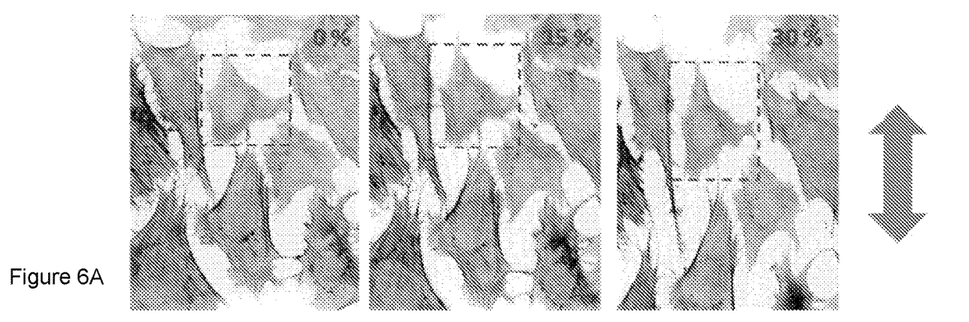
FIGS. 6a and 6b show the results of high resolution imaging of lifeact-RFP transfected U2OS cells under uniaxial stretch.
Figure 6B:
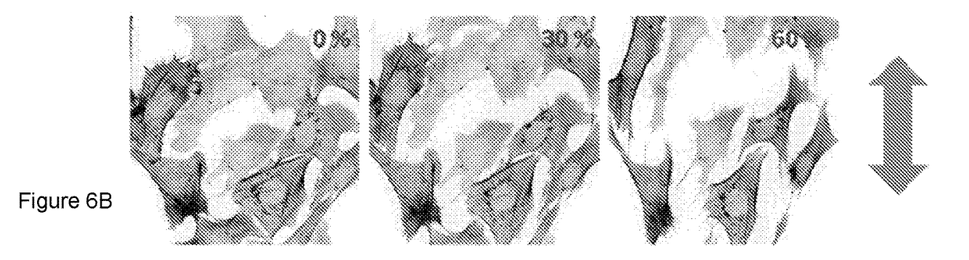
Figure 7A:
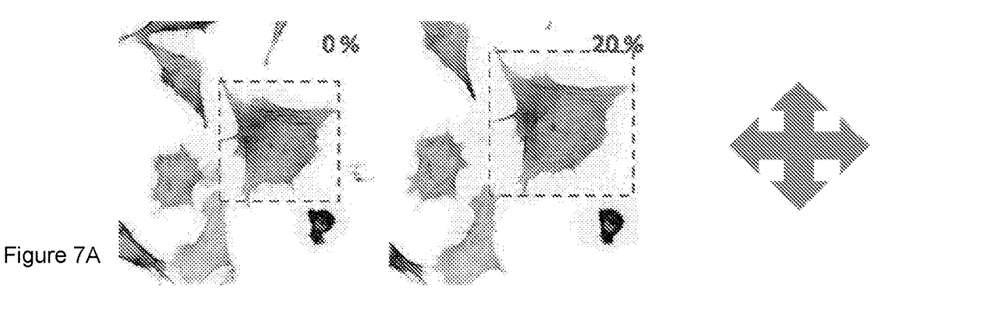
FIGS. 7a and 7b show the results of high resolution imaging of lifeact-RFP transfected U2OS cells under biaxial stretch.
Figure 7B:
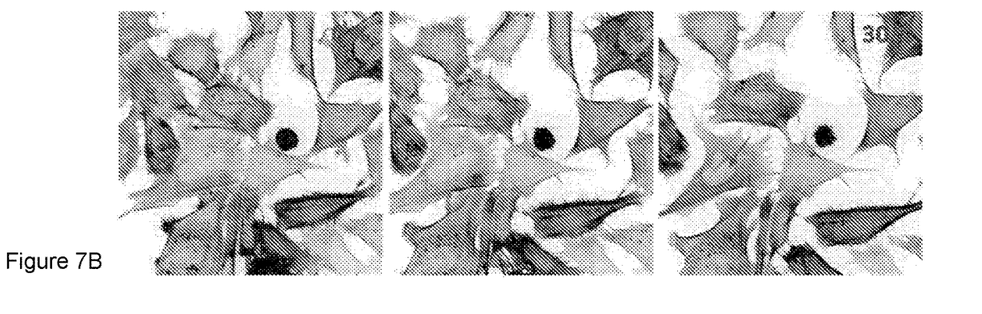
Figure 8A:
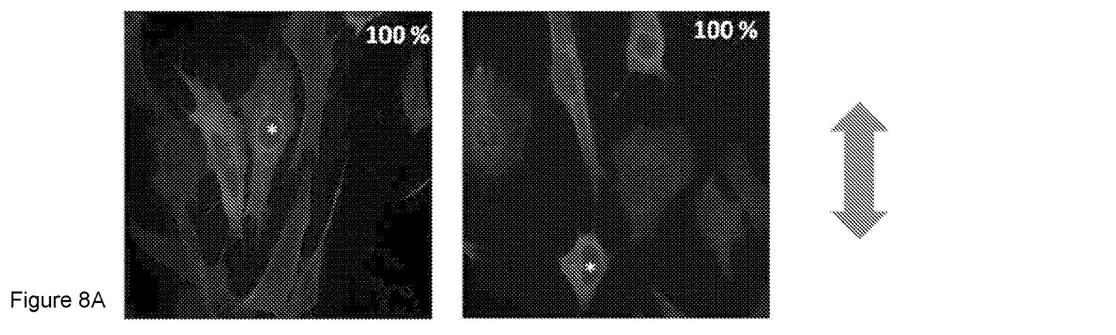
FIGS. 8a and 8b show the results of high level of cell stretching under uniaxial (a) and biaxial (b) stretch.
Figure 8B:
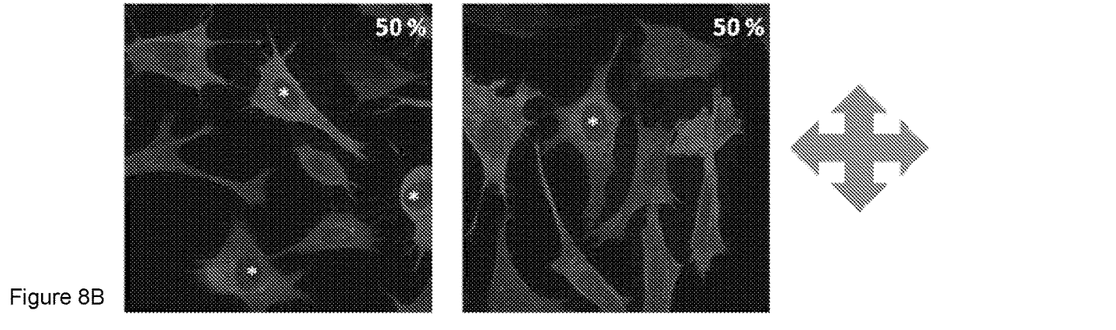

High resolution imaging of lifeact-RFP transfected U2OS cells are shown in FIGS. 6 and 7. Dual function is demonstrated as uniaxial stretch in FIG. 6 and biaxial stretch in FIG. 7. The cell stretching device 1 is further validated by high level of stretch (30%, 50% and 100%) inducing perinuclear actin rim formation (Shao, Li et al. 2015, Proc Natl Acad Sci USA 112(20): E2595-601), as shown in FIGS. 7*b* and 8. The cell stretching device 1 is also validated by a different cell system MCF10A, which form cell monolayer and are stretched as shown FIG. 9.

FIG. 6 shows high resolution images of uniaxial (linear) stretching of U2OS cells transfected with lifeact (actin): A) from 0 to 15% and 30% strain, red dash rectangle marked the boundary of one cell for example; B) from 0% to 30% and 60% strain. Cells are elongated along the vertical stretching axis.

FIG. 7 shows high resolution images of biaxial (isotropic) stretching of U2OS cells transfected with lifeact: A) from 0 to 20% strain, red dash rectangle marked the boundary of one cell for example; B) from 0% to 15% and 30% strain, cell forms perinculear actin rim at 30% strain (accompanied by shrinkage of cell bounday) as indicated by red row in the right panel, which is consistent with previous study (Shao, Li et al. 2015, Proc Natl Acad Sci USA 112(20): E2595-601).

FIG. 8 shows high level of stretching (A. 100% uniaxial strain and B. 50% biaxial strain) induce perinuclear actin rim formation as indicated by white asterisk. Previous study showed that mechanical force application at cell boundary using a AFM tip induced perinuclear actin rim formation (Shao, Li et al. 2015, Proc Natl Acad Sci USA 112(20): E2595-601). High level of stretching experiment recapitulates this cell response.

Figure 9A:
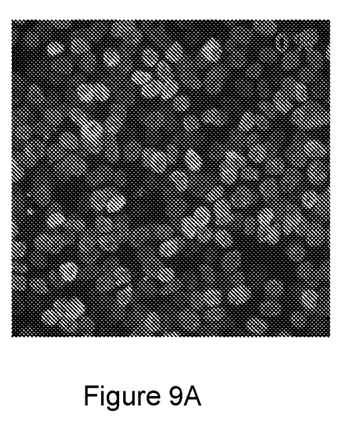
FIGS. 9a and 9b show the results of stretching for MCF10A cells under biaxial stretching.
Figure 9B:
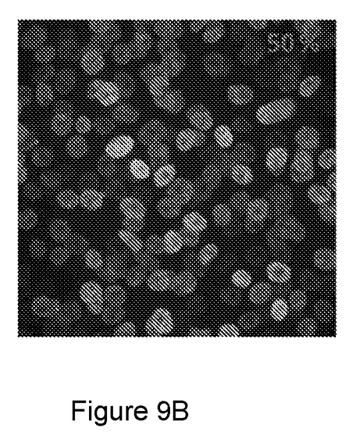

FIG. 9 shows MCF10A cells forming monolayer (transfect with H2B GFP) are stretched, which is reflected by enlargement of nucleus.

Figure 10A:
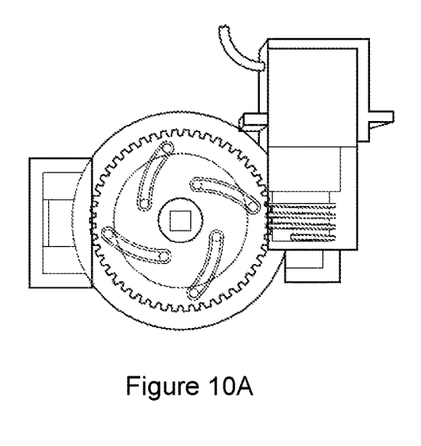
FIG. 10 shows the motorized cell stretching dish. A) Programmable motor was connected to the turning knob 33 to drive the cell stretching dish automatically. B) Examples of typical cyclic stretching function. C) Time lapse images of MCF10A cells (nucleus labeled by H2B-GFP) undergo cyclic stretch (10% strain @ 0.1 Hz as demonstrated in the B) upper panel)
Figure 10B:
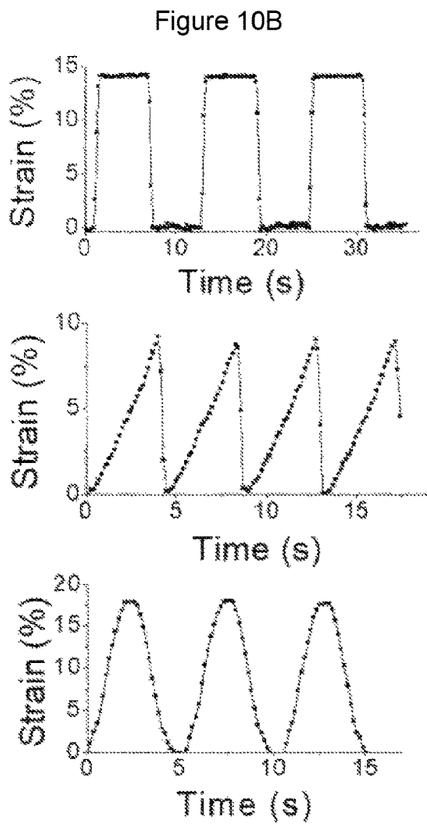
Figure 10C:
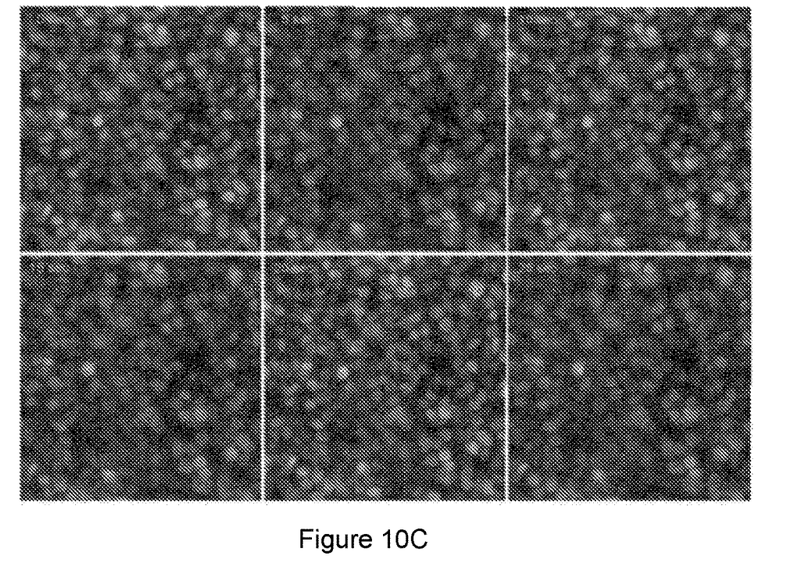

FIG. 10 shows the motorized cell stretching dish. Panel A) shows that the programmable motor was connected to the turning knob 33 to drive the cell stretching dish automatically. Panel B) refers to Examples of typical cyclic stretching function. Panel C) shows time lapse images of MCF10A cells (nucleus labeled by H2B-GFP) undergo cyclic stretch (10% strain @ 0.1 Hz as demonstrated in the B) upper panel).

Figure 11A:
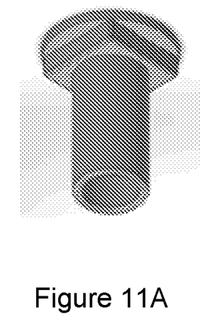
FIG. 11 shows the membrane support pillar. A) Drawing of a hollow support pillar B) Schematic of the set up of the membrane support pillar with the membrane chamber.
Figure 11B:
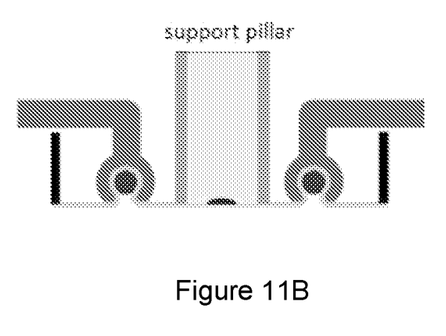

FIG. 11 shows the membrane support pillar to support the membrane and maintain it on perfect focus for high resolution live cell imaging. Panel A) is a drawing of a hollow support pillar. Panel B) is a schematic set up of the membrane support pillar with the membrane chamber.

Whilst features have been presented in combination of the above description, this is intended solely as an advantageous combination. The above description is not intended to show required combinations of features, rather it represents each of the aspects of the disclosure. Accordingly, it is not intended that any described specific combination of features is necessary for the functioning of the cell stretching device and/or the kit for cell stretching.

The invention claimed is:

1. A cell stretching device comprising:
   a cell chamber having an upper portion and a lower portion, wherein the lower portion of the chamber comprises fixing means for fixing a deformable cell substrate (S) to the cell chamber and defining a stretching region inside the chamber at the lower portion, and the upper portion comprises stretching means movable relative to the chamber and acting on the cell substrate (S) and a support element for holding the stretching means; and
   a driving unit coupled to the upper portion of the cell chamber and engageable to the stretching means for mechanically controlling and regulating the movement of said stretching means relative to the cell chamber,
   wherein the stretching means comprise clip members operating inside the stretching region, the clip members being configured to clamp the cell substrate (S) at a clamping contact point and to stretch said cell substrate (S) in response to the movement of the stretching means relative to the cell chamber, and wherein the stretching means comprise one or two pairs of opposing arms configured to move apart from each other according to a linear movement in an opposite direction toward an edge of the stretching region to provide uniaxial and biaxial stretching to said cell substrate (S), wherein the one pair of opposing arms provides uniaxial stretching, and the two pairs of opposing arms provides uniaxial or biaxial stretching.

2. The cell stretching device according to claim 1, wherein the clip members are formed by a clamp element and a removable pin engageable with the clamp element.

3. The cell stretching device according to claim 1, wherein the clip members are located in part inside the cell chamber and interact with only the side of the cell substrate (S) facing inward the cell chamber (S).

4. The cell stretching device according to claim 1, wherein each arm is L-shaped having a first extremity fixable to the support element of the cell chamber and a second extremity comprising the clip member.

5. The cell stretching device according to claim 1, wherein the stretching means are detachable from the cell chamber.

6. The cell stretching device according to claim 1, wherein the driving unit comprises driving means to be actuated by a user or by a motor for producing a driving movement and transfer means coupled to the driving means to transfer the driving motion to the stretching means;

wherein the driving means further comprises a turning knob provided with a worm gear and a cogged ring engageable with the worm gear; and wherein the transfer means further comprises a pair of slidable hinges and a coupling supporting element, each hinge having an extremity fixable to the driving means and the other extremity fixable to the corresponding stretching means.

7. The cell stretching device according to claim 1, wherein the fixing means comprise a cylindrical ring and a hoop engageable with the ring in order to fix the cell substrate (S) to the cell chamber so that the substrate (S) is planar and under tension.

8. The cell stretching device according to claim 1, further comprising a membrane support pillar configured to support said cell substrate (S) and to maintain said cell substrate (S) in focus for high resolution imaging.

9. A kit for cell stretching comprising a cell stretcher device according to claim 1 and a stretchable cell substrate (S) for growing cultured cells.

* * * * *